United States Patent [19]

Fischer et al.

[11] Patent Number: 5,731,581
[45] Date of Patent: Mar. 24, 1998

[54] APPARATUS FOR AUTOMATIC IDENTIFICATION OF GAS SAMPLES

[75] Inventors: Russell John Fischer, Summit; Clement Lim Yu, Plainsboro, both of N.J.; Patrick Francis Crane; Stephen Daniel Walker, both of Boulder, Colo.

[73] Assignee: Ohmeda Inc., Liberty Corner, N.J.

[21] Appl. No.: 403,161

[22] Filed: Mar. 13, 1995

[51] Int. Cl.$^6$ ............ G01N 21/35; G01N 21/17
[52] U.S. Cl. ............ 250/339.13; 250/339.02; 250/343
[58] Field of Search ............ 250/339.02, 339.07, 250/339.12, 339.13, 343, 373; 356/419, 437, 438, 439

[56] References Cited

U.S. PATENT DOCUMENTS

| | | | |
|---|---|---|---|
| 3,696,247 | 10/1972 | McIntosh et al. | 250/339.13 X |
| 3,860,344 | 1/1975 | Garfunkel | 250/339.13 X |
| 3,973,118 | 8/1976 | LaMontagne | 250/339.02 X |
| 3,976,883 | 8/1976 | Krakow . | |
| 4,054,389 | 10/1977 | Owen | 356/419 |
| 4,157,470 | 6/1979 | Kotaka et al. . | |
| 4,158,772 | 6/1979 | Reedy . | |
| 4,180,734 | 12/1979 | Gedeon . | |
| 4,200,791 | 4/1980 | Burough . | |
| 4,467,203 | 8/1984 | Rappaport . | |
| 4,694,173 | 9/1987 | Wong . | |
| 4,888,484 | 12/1989 | Harvey . | |
| 4,914,719 | 4/1990 | Conlon et al. | 250/343 |
| 4,928,015 | 5/1990 | Butler et al. . | |
| 4,957,371 | 9/1990 | Pellicori et al. . | |
| 5,046,018 | 9/1991 | Flewelling et al. . | |
| 5,081,998 | 1/1992 | Yelderman et al. | 250/339.02 X |
| 5,092,342 | 3/1992 | Hattendorff et al. . | |
| 5,159,199 | 10/1992 | LaBaw | 250/339.02 |
| 5,166,755 | 11/1992 | Gat | 356/419 |
| 5,296,706 | 3/1994 | Braig et al. | 250/339.13 |
| 5,360,004 | 11/1994 | Purdy et al. . | |
| 5,379,764 | 1/1995 | Barnes et al. . | |
| 5,440,143 | 8/1995 | Carangelo et al. . | |
| 5,460,177 | 10/1995 | Purdy et al. . | |

OTHER PUBLICATIONS

Richardson et al., "A Novel Infrared Spectrometer Using a Linear Array Detector", Applied Spectroscopy, vol. 44, No. 5, 1990, pp. 822–825.

Maris et al., "Nonlinear Multicomponent Analysis by Infrared Spectrophotometry", Anal. Chem., 1983, 55, pp. 1694–1703.

*Primary Examiner*—Edward J. Glick
*Attorney, Agent, or Firm*—Roger M. Rathbun; William A. Schoneman; Thomas R. Marsh

[57] ABSTRACT

The gas sample identification apparatus transmits at least one beam of light of predefined frequency band through a gas sample present in a gas sampling chamber. The presence and concentration of various agents in the gas sample are determined by a linear variable filter that selectively passes the light beam transmitted through the gas sample chamber to an array of detectors. The detectors are positioned to receive only a narrow passband component of the light beam. The output signals from the array of detectors is processed by a multivariate statistical processor to accurately identify both the presence and concentration of one or more agents contained in the gas sample.

24 Claims, 4 Drawing Sheets

APPARATUS FOR AUTOMATIC IDENTIFICATION OF GAS SAMPLES

FIELD OF THE INVENTION

This invention relates to apparatus that is used to accurately identify component(s) contained in a gas sample and their concentrations, for example, the concentration of respiratory and anesthetic gases contained in respiratory gas samples obtained from an anesthetized patient.

PROBLEM

It is a problem in the field of medical monitoring equipment to produce an apparatus for measuring the concentration of anesthetic agents in a respiratory gas sample that is inexpensive, simple to use, very accurate, fast in its measurements and yet adaptable to measure new anesthetic agents that are introduced to the field of anesthesiology. In the field of anesthesiology, there are four commonly used anesthetic agents: nitrous oxide, halothane, enflurane and isoflurane. Most existing infrared anesthetic agent monitoring apparatus operate by measuring the optical transmissivity of a respiratory gas sample at four wavelengths of light. The resultant measurements are processed using matrix mathematics to identify a single one of these four anesthetic agents that is contained in the gas sample as well as its concentration.

Existing infrared anesthetic agent monitoring apparatus generally perform two functions: a first that identifies the anesthetic agent that is present in the respiratory gas sample, and a second that determines the concentration of the identified anesthetic agent in the respiratory gas sample. These two functions may be performed either by two separate sets of circuitry in the apparatus or by a common set of circuitry. These apparatus are determined systems, with the number of spectral filters used therein being equal to the number of anesthetic agents that the apparatus is designed to identify. The selection of the wavelengths passed by the spectral filters is driven by the desire to use wavelengths that are strongly and uniquely absorbed by the anesthetic agents in question. Beer's Law (A=ECL) teaches that the light absorbance exhibited by a respiratory gas sample is substantially linearly related to the concentration of the anesthetic agent contained in the respiratory gas sample. Since the terms E and L in this equation are constants, the presence and partial pressure of the anesthetic agent are determined by monitoring wavelength specific light absorbance values. If each anesthetic agent absorbed energy at only one of the selected wavelengths, the analytical task is simple in that the concentration of each anesthetic agent linearly follows the light absorbance measured at that one wavelength. However, anesthetic agents are chemically similar and their absorbance spectra generally overlap, exhibiting varying degrees of colinearity. This lack of absorbance uniqueness necessitates measuring light absorbance of the respiratory gas sample at all of the selected wavelengths to identify and quantify the anesthetic agent contained in the respiratory gas sample.

A basic limitation of existing determined infrared anesthetic agent monitoring apparatus is that they do not examine enough spectral wavelengths to accurately identify anesthetic agents when the respiratory gas sample includes common contaminants, such as alcohol and methane, whose absorbance spectra overlap those of anesthetic agents. This problem arises because the number of analytes (anesthetic agents plus contaminants) exceeds the number of spectral measurements available to the anesthetic agent monitoring apparatus, thereby rendering the anesthetic agent monitoring apparatus an underdetermined system. In addition, the introduction of a new anesthetic agent forces a redesign of the anesthetic agent monitoring apparatus, which becomes an underdetermined system in the face of a broader set of anesthetic agents.

In addition, the prior art anesthetic agent monitoring apparatus do not measure the concentration of $CO_2$ gas in the respiratory gas sample. Separate apparatus is routinely provided to perform this measurement.

SOLUTION

The above described problems are solved and a technical advance achieved in the field by the apparatus and method for the automatic identification of gas samples of the present invention which utilizes a new architecture to accurately identify analytes contained in a gas sample and their respective concentrations. One application of this apparatus is to identify anesthetic agents contained in a respiratory gas sample as well as their relative concentrations. This apparatus transmits at least one beam of light of predetermined frequency band through a respiratory gas sample that is passed through a gas sample chamber. This frequency band is selected to contain unique spectral signatures from all the analytes of interest. The presence and concentration of both carbon dioxide ($CO_2$) and the anesthetic agents in the respiratory gas sample are determined by the use of an optical path that, in one embodiment of the invention, includes a variable filter that passes selected wavelength components (7–10 microns) of the light beam that is transmitted through the gas sample chamber to an array of light detectors. The light detectors are each positioned with respect to the variable filter to receive only a narrow passband component of the light beam that is transmitted through the gas sample chamber. A processor receives the output signals from the array of light detectors and accurately identifies both the presence and concentration of one or more anesthetic agents contained in the respiratory gas sample.

This apparatus simultaneously measures anesthetic agents and $CO_2$. The $CO_2$ signals are provided by a dedicated detector(s) which underlies a separate $CO_2$ filter which abuts the variable filter. This dedicated detector is optically segregated from the detectors which service the linear variable filter, but it can remain part of a singular detector array. An alternative to the use of two filters is the use of selected wavelength components for $CO_2$ and anesthetic agents that span a single band, such as 3–5 microns. The processor uses a multi-variate statistical technique to precisely differentiate among the numerous anesthetic agents. In particular, the anesthetic agent monitoring apparatus uses partial least squares as the computation method. This method has advantages over other computational techniques in that the regression coefficients and predicted concentrations for each analyte can be computed independent of each other. In addition, the partial least squares technique is better suited to predict analyte concentration in the presence of nonlinearities. The partial least squares method is implemented in the gas sample identification system, which is an "overdetermined" system and provides a surfeit of spectral information during each sample period by use of a variable filter tuned to a spectrally rich region to provide useful (high signal to noise ratio) information. An overdetermined system, one that examines more wavelengths than analytes, has more spectral information available and is better able than a determined system to resolve subtle distinctions between the absorbance spectra of chemically similar analytes. The overdetermined system processes the pattern of spectral measurements which results from the unique spectral signature of the anesthetic agent, rather than seeking a single unique feature of the spectral signature of the anesthetic agent. This anesthetic agent monitoring apparatus provides synchronous acquisition of the entire spectrum of interest, which allows for quicker and more accurate identification and quantification of anesthetic agents contained in a respiratory gas sample.

A training set of anesthetic agents and combinations of anesthetic agents is presented to the automatic gas sample identification apparatus to generate data, indicative of the combination of output signals from the light detectors for the specific anesthetic agent or combination of anesthetic agents. The processor uses this data to create a calibration set which is used in subsequent measurements to identify the anesthetic agent present in the respiratory gas sample and its concentration by comparing the present measurement with the calibration set. The processor can adapt to new inputs by providing a new calibration set and can thereby extrapolate its knowledge to cover new anesthetic agents and concentrations of anesthetic agents without requiring modification of the apparatus. The noted anesthetic agents have strong absorbance at the selected range of wavelengths and a new anesthetic agent is likely to also have strong absorbance in this range.

DETAILED DESCRIPTION

Figure 1:
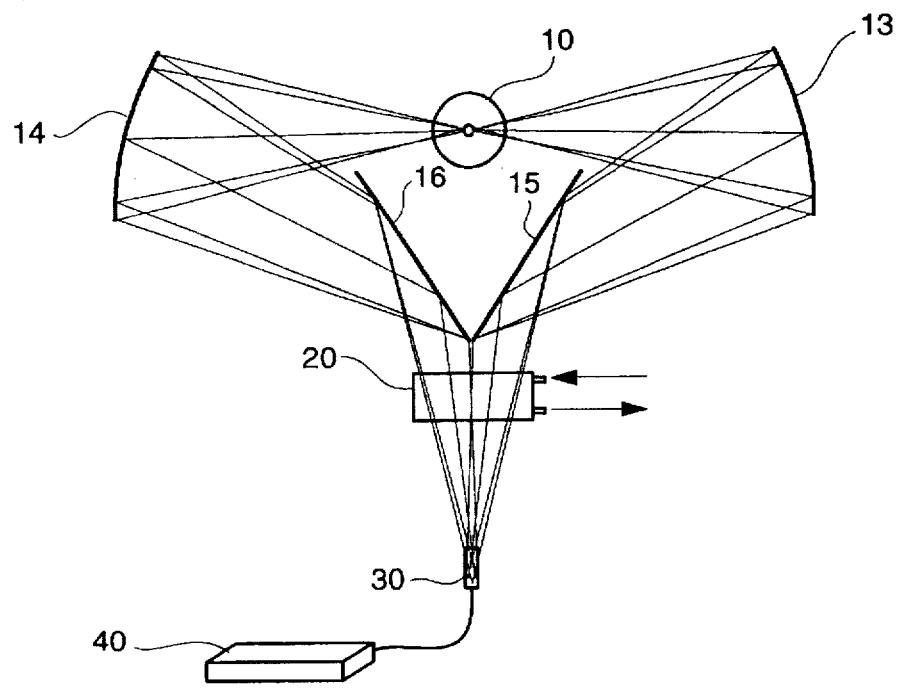
FIG. 1 illustrates, in block diagram form, the overall architecture of the automatic gas sample identification apparatus of the present invention.
Figure 2:
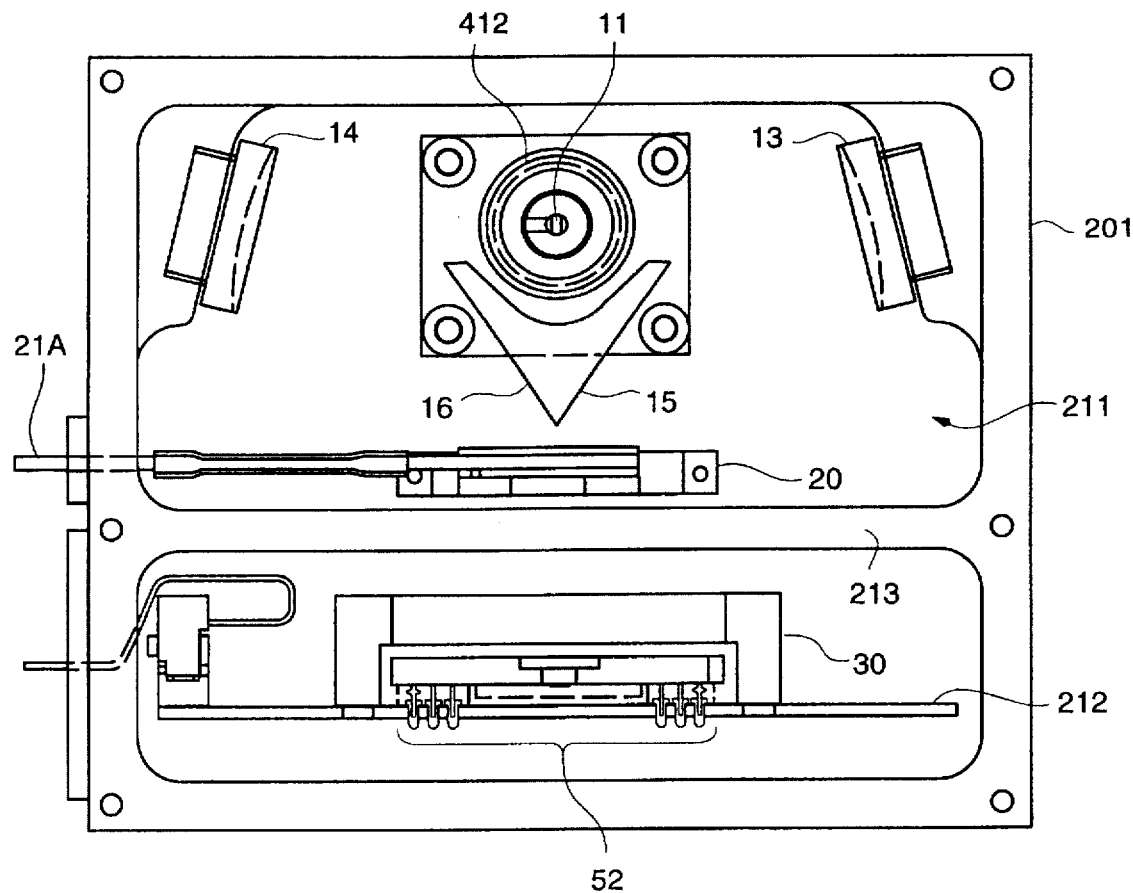
FIG. 2 illustrates additional implementation details of the automatic gas sample identification apparatus via a top view of the apparatus.

FIG. 1 illustrates in block diagram form the overall system architecture of the apparatus for the automatic identification of gas samples, while FIG. 2 illustrates additional implementation details of this apparatus. This gas sample identification apparatus 1 functions to both detect the presence and measure the concentration of analytes contained in a gas sample that is passed through a gas chamber 20. The anesthetic agent monitoring system apparatus that is described herein as the preferred embodiment of the invention represents one application of this inventive concept, and the overall architecture of this gas sample identification apparatus 1 is equally applicable to other applications where one or more analytes are contained in a gas sample, and the presence and concentration of these analytes must be determined with accuracy.

Basic System Architecture

In FIG. 1, the gas sample identification apparatus 1 is illustrated as including a light source 10, mirrors 13–16, gas chamber 20, detector circuit 30 and computation circuit 40. In operation, a gas sample is passed through gas chamber 20 while at least one beam of light produced by light source 10 is transmitted through the gas chamber 20. The gas sample has optical transmissivity characteristics that are determined by the type of components contained in the gas sample as well as their concentrations. Therefore, the light beam that passes through the gas sample in gas chamber 20 is optically processed by various filter and detector elements contained in detector circuit 30 to produce electrical signals that can be used by computation circuit 40 to precisely identify the components contained in the gas sample as well as their relative concentrations. In the application of this apparatus to anesthetic agent monitoring, respiratory gases obtained from an anesthetized patient are passed through gas chamber 20 to identify the presence and concentration of carbon dioxide ($CO_2$) as well as the presence and concentration of one or more anesthetic agents in the patient's respiratory gases. These measurements must be very accurate in both the identification of the anesthetic agents in use and the concentration of these agents to avoid injury to the patient.

In the field of anesthesiology, there are four commonly used anesthetic agents: nitrous oxide, halothane, enflurane and isoflurane. Additional new anesthetic agents: desflurane and sevoflurane, are being introduced. Therefore, the detector circuit 30 and computation circuit 40 must have the capability to measure subtle differences in optical transmissivity in the gas sample to distinguish between the various anesthetic agents and combinations of anesthetic agents used in various concentrations.

Gas Sample Identification Apparatus Housing

FIG. 2 illustrates additional implementation details of a portion of the gas sample identification apparatus 1. The gas sample identification apparatus 1 is typically installed in a housing 201 that functions to provide an enclosure that protects the elements of gas sample identification apparatus 1 from the ambient environment. The housing 201 is manufactured from a material, such as aluminum, that has a low level of outgassing and also provides dimensional stability over a wide range of temperatures. The housing 201 also functions as a rigid substrate to which the various elements of the gas sample identification apparatus 1 are secured and positioned. The top view of the gas sample identification apparatus 1 of FIG. 2 is of the housing 201 with its cover plate removed. The housing 201 is segmented into two sections, 211, 212. The first section 211 houses the optical elements 11–16 and the gas chamber 20, while the second section 212 houses the light detector 30 and at least some of computation circuit 40. A bulkhead 213 forms the common wall of the first 211 and second 212 sections and functions to provide a barrier that limits the transfer of stray light from the first section 211 to the second section 212.

Light Source

Figure 5:
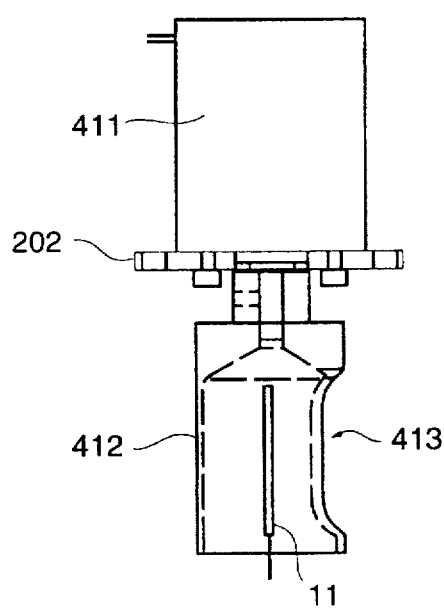
FIG. 5-6 illustrate, in side view, the light generation apparatus.
Figure 6:
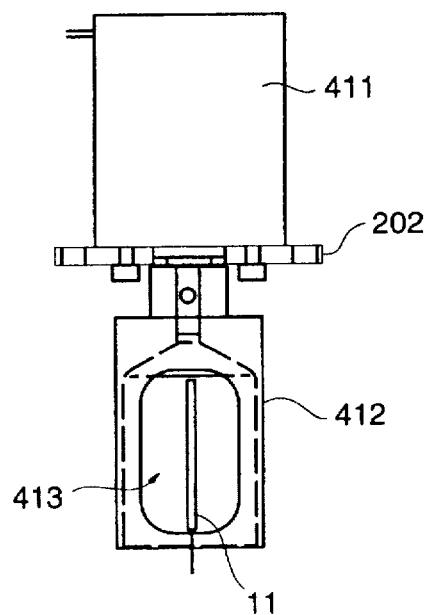

FIGS. 5 and 6 illustrate two side views of the light source 10 used in this gas sample identification apparatus 1. The light source 10 comprises a "blackbody" source of infrared light 11, mounted in housing 201 of FIG. 2. Infrared source 11 is surrounded by a drum shaped chopper 412, which is mounted on the cover plate 202 of housing 201, and produces a light beam of the desired band of wavelengths of light. The infrared source 11 is a featureless "bar" shaped element that has two flat, 180° opposed emissive surfaces to thereby produce two light beams, transmitted in opposite directions from infrared source 11. The image of source 11 is transmitted by mirrors 13–16 to the gas chamber 20 so the use of a featureless flat source maximizes the uniformity of the light beam applied to gas chamber 20. The infrared source 11 is manufactured from a material such as silicon nitride which, when heated to an operating temperature of approximately 800°–900°, functions as a blackbody source of infrared light in the 4 to 12 micron wavelength range of interest.

The chopper 12 comprises a motor 411 attached by a shaft to chopper drum 412, which includes at least one aperture 413 formed therein. When the chopper drum 412 rotates, the two light beams that emanate from infrared source 11 are alternately transmitted by the aperture 413 which passes the light beams to a corresponding one of spherical mirrors 13, 14. The aperture 413 is substantially rectangular in shape, with rounded corners. The size and shape of aperture 413 are such that for 25% of the rotational cycle time of chopper drum 412, the gas sample chamber 22a is illuminated, followed by a dark time that is 25% of the cycle time, followed by illuminating the reference chamber 22b for 25% of the cycle time, followed by a dark time that is 25% of the cycle time.

The spherical mirrors 13, 14 focus the light beam received from chopper drum 412 on to flat mirrors 15, 16, respectively. The flat mirrors 15, 16 produce light beams of narrow angular dispersion which are applied to gas sample chamber 22a and reference chamber 22b, respectively of gas chamber 20. This configuration ensures that the incident angle of the light beam on the chambers 22a, 22b is maintained at a small value, typically less than 15°. The mirrors 13–16 are manufactured from a thermally stable highly reflective material, such as polished aluminum. These mirrors must reflect infrared wavelengths, and maintain their alignment, which requirement is simplified by the fact that the housing and mirrors are manufactured from the same material, thereby eliminating inconsistent thermal characteristics as a factor.

Anesthetic Agent Detector-Optical Processing

Figure 7:
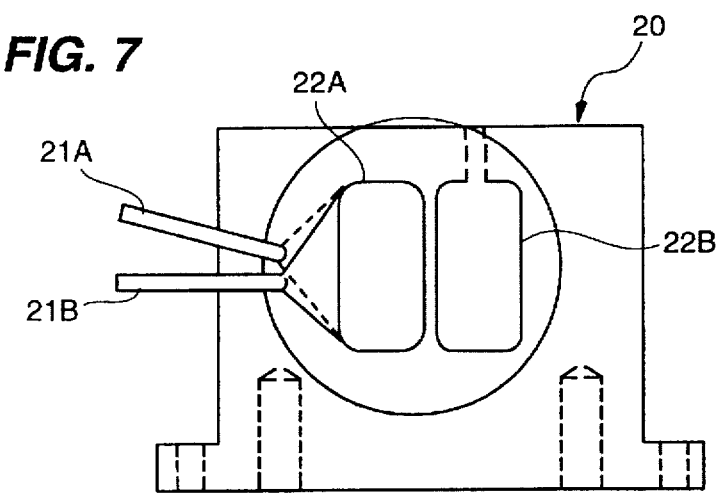
FIGS. 7 and 8 illustrate a top view and a side exploded view, respectively, of the gas sample and reference chambers.
Figure 8:
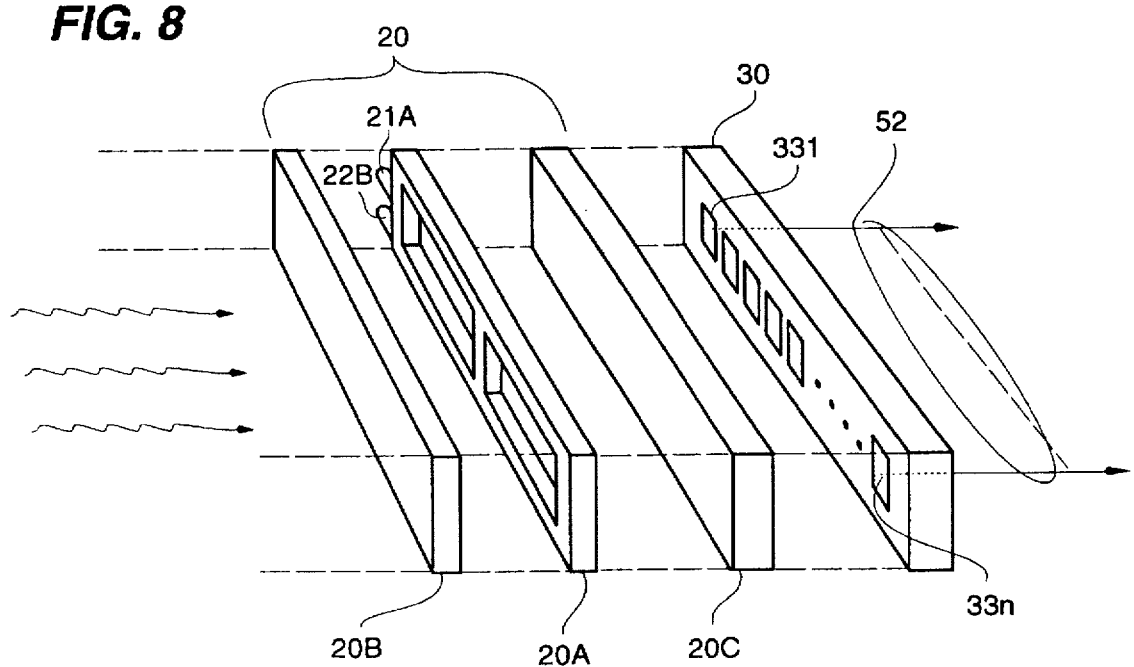

FIG. 7 illustrates a top view of gas chamber 20 and FIG. 8 illustrates an exploded view. The gas chamber consists of a gas sample chamber 22a and a reference chamber 22b positioned coplanar and side by side. Gas chamber 20 consists of a frame 20a to which is attached barium fluoride window 20b to admit light to both sections 22a, 22b of only the wavelengths within the range of 0–12 microns. Also attached to frame 20a, on a side opposite window 20b, is barium fluoride window 20c. The combination of frame 20a, windows 20b, 20c creates a sealed reference chamber 22b, having a port that is open to the ambient pressure and atmosphere inside of housing 201. The reference chamber 22b can alternatively be evacuated or contain selected gases that do not absorb at the wavelengths of interest for the gas sample chamber 22a. The two identical light beams that emanate from light source 10 traverse identical optical paths through the gas sample identification apparatus 1. The only difference in the light paths is that reference chamber 22b does not contain a respiratory gas sample, while the gas sample chamber 22a does. By measuring the light intensity of the light beam that traverses reference chamber 22b, the apparatus can establish a baseline reference for the absorbance value at the selected wavelengths, since the two optical paths are identical except for the presence of the respiratory gas sample. The concentration of the respiratory gas sample present in the gas sample chamber 22a is determined by computing the ratio of the log of the intensity of the light beam passed through the reference chamber 22b to the log of the intensity of the light beam passed through the gas sample chamber 22a.

The combination of frame 20a, windows 20b, 20c also creates sealed gas sample chamber 22a, having an inlet port 21a and an outlet port 21b at one end. The respiratory gas from a patient enters gas sample chamber 22a via inlet port 21a and passes along the entire length of the gas sample chamber 22a juxtaposed to window 20b, then along window 20c, to outlet port 21b where it exits. The gas inlet port 21a and gas outlet port 21b provide constant cross sectional area along their length and change shape gradually to a final flat fan shaped aperture as the port enters the gas sample chamber 22a to thereby spread the gas sample uniformly along the entire width of the window 20b. The gas sample is irradiated along the entire length of gas sample chamber 22a by one of the two identical light beams produced by light source 10.

In determining the configuration of the optical elements of gas sample identification apparatus 1, it is important to note that the spectral content of the light used and the spectral resolution of the individual pixels are major design considerations. The wavelengths of light used should preferably encompass some unique absorbance patterns of the target analytes while also covering a range where contaminants have low absorbance. The number of detectors is a function of the number of spectral measurements required to uniquely identify the set of components of interest. Acquiring additional spectral features of a gas sample provides increased analytical power, but since the entire absorption spectrum is concurrently gathered from a single respiratory gas sample, the number of detectors is also a function of decreased signal to noise on individual detectors. Furthermore, the larger the number of spectral samples, the greater the size of the gas sampling chamber (span of the linear variable filter) and the slower the response time due to latency in gas transfer through the gas sample chamber 22a. The path length of the gas sample chamber 22a is selected as a function of the components being measured. The path length should be long enough to enable lightly absorbing components to cause a measurable change in intensity yet not enabling highly absorbing components to absorb substantially all the incident light at selected wavelengths. With regard to spectral resolution, the pixel bandwidth is defined by: the design of the linear variable filter, the pixel width, the proximity of the detector to the filter, and the angle of incidence of the light on the detector. The pixel bandwidth selected for this application is 0.69% of the centered wavelength. It is important to maintain a high spectral resolution to minimize deviations from Beer's Law and to retain the distinguishing spectral features of the component of interest. The spectral resolution can be increased by narrowing the pixel width, but this results in less incident light for each detector and can reduce the signal to noise ratio.

Detector

Figure 3:
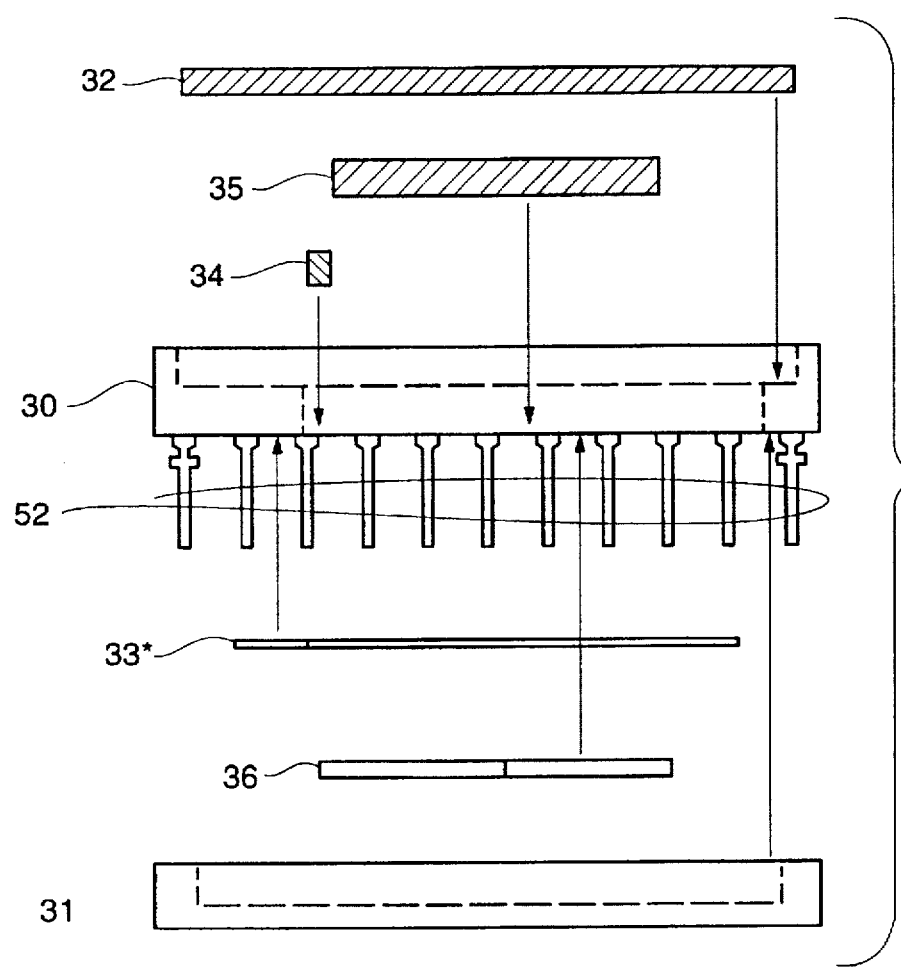
FIGS. 3 and 4 illustrate, in exploded block diagram form, said side view, respectively, an embodiment of the light detector apparatus.
Figure 4:
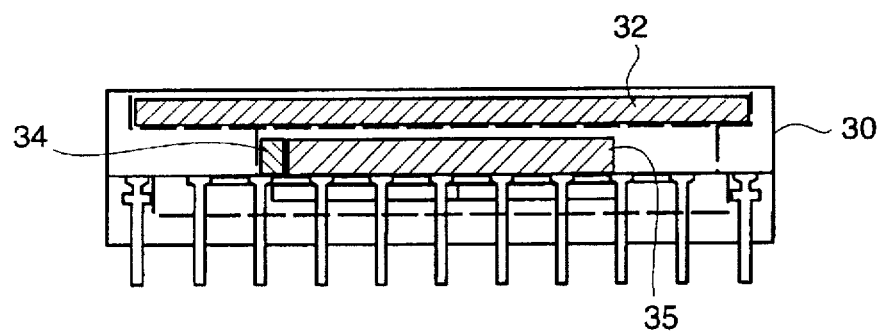

FIGS. 3 and 4 illustrate side exploded and side views, respectively of the light detector apparatus 30. The light detector apparatus 30 consists of a ceramic package 31, into which are mounted a number of elements. A blocking filter 32 manufactured from optical grade germanium seals the package and passes light of wavelengths from 4–12 microns. Mounted below blocking filter 31 are two filter elements: $CO_2$ filter 34 and a variable filter 35 which is abutted to the $CO_2$ filter 34. The $CO_2$ filter 34 is manufactured from optical grade sapphire and passes a narrow band of light centered around the wavelength 4.26 microns, which is representative of the absorption spectrum of $CO_2$. The variable filter 35 consists of a structure that creates a spatially varying filter characteristic in the wavelength range of 7–10 micron range.

Thus, the physical position of each detector placed behind the varying filter 35 determines the selected passband component of the frequency band that is detected by the detector. In the preferred embodiment disclosed herein, a substantially linearly varying filter characteristic is selected to produce the measurements at the selected passbands of interest. This can be accomplished in a number of ways, preferably using a wedge-filter that is constructed of alternating layers of high and low diffractive index selectively deposited on a transparent substrate. The thicknesses of these layers are tapered in a controlled manner to create a two-dimensional interference filter of precisely controlled varying characteristics. Alternatively, a plurality of bandpass filters configured into a linear array can be used, with, as in this preferred embodiment, one end of linear bandpass filter 35 passing light from wavelength 7.2 micrometers to the other end of linear variable filter 35 which passes light up to a wavelength 9.8 micrometers, as a function of position along the length of linear variable filter 35. The variable filter 35 allows light to exit gas sample chamber 22a only if the wavelength of light matches the filter characteristic of variable filter 35 at that particular locus. Thus, by placing detectors 33₁-33n at various sites along the length of variable filter 35, narrow passbands of light centered around selected wavelengths can be detected (herein referred to simply as "wavelengths"). The locus of each detector defines the wavelength of light that is received from gas sample chamber 22a. The number of wavelengths of light detected is simply a function of the number of light detectors 33₁-33n placed along the length of linear variable filter 35. To detect an additional passband of light simply requires the addition of another detector 33* at a site that corresponds to the desired wavelength of light. This configuration of elements minimizes the complexity of the apparatus and enables additions and changes to be made with relative simplicity. The signals produced by the detectors 33₁-33n are output on signal leads 52 for further processing to identify both the presence and concentration of the various gas samples, as is described below.

The array of detector elements 33* mounted below the $CO_2$ filter 32 and linear variable filter 35 functions to produce a signal of magnitude proportional to the intensity of the light incident on each detector element 33* in the array. The light incident on each detector 33* in the array is a function of the position of the detector 33* below the respective one of $CO_2$ filter 34 and linear variable filter 35. Also included in the light detector apparatus 30 are, optionally, preamplifier circuits 36, which function to condition the signals generated by the detectors 33* for transmission via leads 52 to the computation circuit 40.

Data Conversion Apparatus

Figure 9:
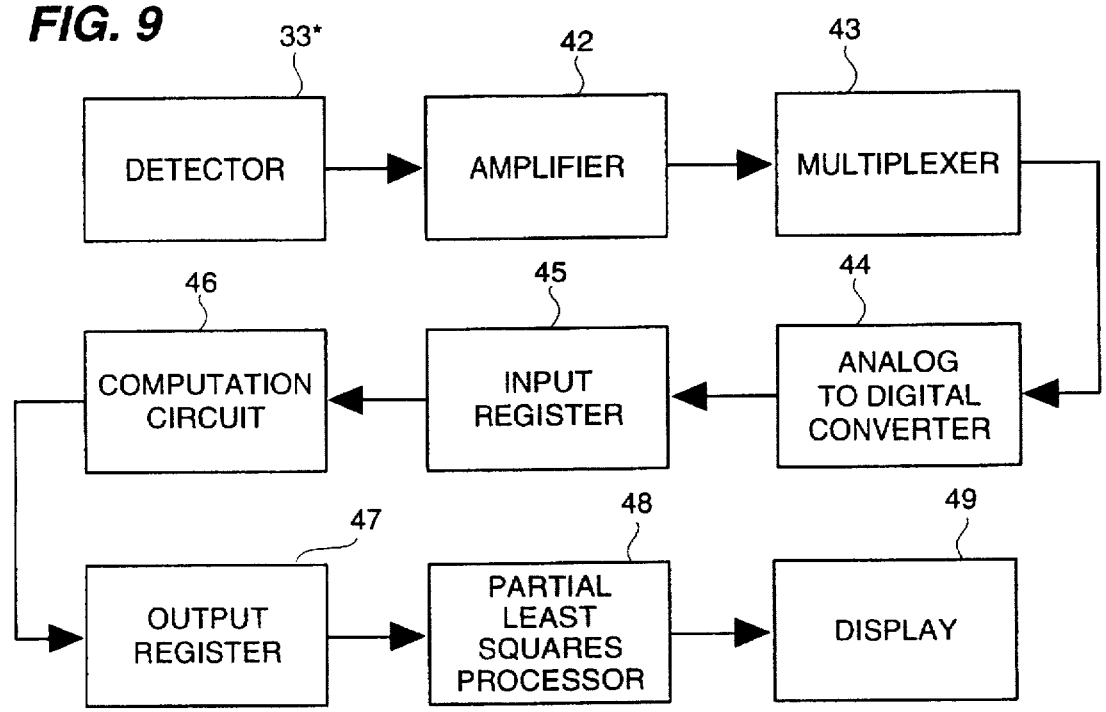
FIG. 9 illustrates in block diagram form the architecture of a data conversion apparatus used in the detector circuit.

The analog signals output by each of the light detectors 33* are applied via leads 52 to a data conversion apparatus that is part of computation circuit 40, and which transforms the analog measurement value output by the light detectors 33* (and conditioned by preamplifier circuits 34) into a digital value that can be used by the computation circuit 40 to perform its determination. In particular, FIG. 9 illustrates in block diagram form the overall architecture of a typical data conversion apparatus wherein the output of detectors 33* are applied to an amplifier 42 having a predetermined gain characteristic to produce a signal of sufficient magnitude for further processing. The amplifier output from each of the detectors 33* is applied under control of processor 46 to analog to digital converter circuits 44 which convert the analog amplified magnitude to a digital representation indicative of the magnitude of the intensity of the light beam that was received by the corresponding light detector element 33*. The digital data that are produced by the analog to digital converters 44 are then loaded into an input register 45 where they are used by a processor 46 to produce digital values indicative of the magnitude of the received light beams. These computed digital values are then loaded into an output register 47 for transmission to additional circuitry in the computation circuit 40 to complete the analysis function.

Detector Sample Processing Considerations

It is well known pursuant to Beer's Law that the absorbance of a component contained in a gas sample is the product of the optical extinction coefficient of the component at the selected wavelength of light used to illuminate the gas sample, multiplied by the concentration of the component in the gas sample, multiplied by the length of the path the light takes through the gas sample. Each component in a gas sample has a unique pattern of light absorbance as a function of wavelength, which is termed its absorption spectrum. Since the absorbance of a component follows Beer's Law, linear analytical techniques can be used to identify and determine the concentration of various components that can be contained in a gas sample. If each of N components absorbed at a distinct wavelength (spectral absorption peak), only N spectral samples need be taken to uniquely determine the presence of any of the N components in a gas sample. However, spectral absorption peaks somewhat overlap among various related components, yet the absorption spectrum of the components are relatively distinct. Thus, by sampling the gas sample using greater than N spectral measurements, sufficient analytical data can be obtained to ensure accurate identification of components contained in the gas sample as well as their concentrations. In the gas sample identification apparatus 1, the spectral samples taken are used by computation circuit 40 to identify the component contained in the gas sample as well as its concentration. The computation circuit 40 uses a multivariate statistical technique to precisely differentiate among the numerous anesthetic agents. In particular, the anesthetic agent monitoring apparatus 1 uses partial least squares as the computation method. This method has advantages over other computational techniques in that the regression coefficients and predicted concentrations for each analyte can be computed independent of each other. In addition, the partial least squares technique minimizes errors in the determination of analyte concentration, which is one of the two measurements performed by the system. The partial least squares technique is capable of learning the absorption spectrum of the components. A linear analytical technique is used during a calibration process to learn the pattern of a component's absorption signature. A training set of anesthetic agents at various concentrations is submitted to the automatic gas sample identification apparatus as part of the calibration process. A predictive analytical model is then generated for these components to enable the computation circuit 40 to extrapolate the training set to whatever combination and concentration of components are included in a gas sample.

Partial Least Squares Method of Spectral Analysis

Partial least squares modeling is a multivariate statistical tool used for quantitative analysis of data. This method is capable of being a full-spectrum method and therefore by having a full spectrum has a signal averaging benefit. Since there is a substantially linear relationship between the measured absorbance and the component concentration in the gas sample, a calibration step is used to determine the relationship between the absorbance spectrum and the component concentration from the training set of calibration samples. The calibration step is followed by a prediction step wherein the results of the calibration are used to predict or estimate the component concentrations in the "unknown" sample present in the gas sampling chamber 20. These operational steps are also used in other multivariate statistical tools, such as classical least squares and multiple linear regression methods. A major disadvantage of classical least squares is that all interfering chemical components in the spectral region of interest need to be known and included in the calibration. A major disadvantage of multiple linear regression methods is that the analysis has to be restricted to a small number of frequencies since the number of frequencies is limited by the calibration mixtures, and increasing the number of frequencies results in an impractically large calibration set. In addition, measurement noise is included in the multiple linear regression methods, so the precision of prediction results is normally worse than partial least squares model. Partial least squares processing eliminates a significant amount of measurement noise through data reduction as discussed later. Partial least squares processing has advantages over other computational techniques in that the regression coefficients and predicted concentrations for each analyte can be computed independent of each other. In addition, the partial least squares technique is better suited to predict analyte concentration in the presence of nonlinearities.

In one embodiment of the partial least squares processor 48, the partial least squares analysis assumes an inverse linear model defined by the matrix equation:

$$c = Ab + e$$

where the term A is the instrument response matrix (such as a collection of spectra) for a series of calibration samples, the term c is a vector with the concentrations of the anesthetic agent of interest for all the calibration samples (here a model is constructed for one analyte at a time), the term b is a regression vector that contains the model parameters, and the term e is a vector of concentration residuals. The partial least squares analysis estimates the regression vector b by calculating an estimate of the pseudo-inverse of the matrix A as follows:

$$\hat{b} = A^{3o} c$$

Estimating the pseudo-inverse matrix in partial least squares analysis is a three-step procedure. First, the response matrix A is decomposed into two matrices as follows:

$$A = TP^T$$

where the columns of the T matrix are orthogonal. The T and P matrices are commonly referred to as the scores and loadings matrices, respectively. The loading matrix P can be further decomposed into two matrices as follows:

$$P = SV^T$$

where the columns of the V matrix are orthogonal and S is a bidiagonal matrix. Therefore, the response matrix A is eventually decomposed into three matrices as follows:

$$A = TSV^T$$

A low dimension approximation through truncation of the matrices is then made so that all the relevant information is retained while the noise is filtered out. Finally, the pseudo-inverse of this approximation is calculated as follows:

$$A+ = \overline{V}\overline{S}^{-1}\overline{T}^T$$

where the bars over the matrices indicate that the matrices are truncated to the optimal pseudo-rank. The pseudo-rank is corresponding to the number of columns in the truncated matrices. The selection of pseudo-rank is important such that the noise in the model is minimized and the predictive ability of the model is optimized. Once the pseudo-inverse of A is calculated during the calibration step, the regression vector b is estimated and the model obtained. Once the model is constructed, it is used for future predictions. The concentration of an analyte of interest in an unknown respiratory gas sample can therefore be estimated by the equation:

$$\hat{c}_{un} = a_{un}^T \hat{b}$$

where $\hat{c}_{un}$ is the estimate of the concentration of the analyte of interest in an unknown sample "un" and $a_{un}$ is the instrument response measured for the unknown sample.

Thus, the data presented to the partial least squares processing system 48 in computation circuit 40 is processed using the above-noted relationship, once the appropriate training set is used to initialize the gas sample identification apparatus 1. The result of this processing is that a specific component contained in the gas sample present in the gas sampling chamber 22a is identified and its concentration determined. The results of this computation are displayed to the user via a display device 49 which presents an identification of the determined component and its concentration in human readable form, such as an alphanumeric readout. The accuracy of the displayed result is a function of the divergence of the gas sample from the set of calibration samples used to initialize the system as well as the degree of nonlinearity present in the system.

While a specific embodiment of this invention has been disclosed, it is expected that those skilled in the art can and will design alternate embodiments of this invention that fall within the scope of the appended claims.

We claim:

1. Apparatus for identifying the concentration of at least one of n anesthetic agent compounds contained in a respiratory gas sample, wherein each said anesthetic agent component has a unique pattern of spectral wavelength absorbance characteristics, n being a positive integer greater than zero, comprising:

a gas sample chamber having an inlet port and an outlet port and through which a respiratory gas sample to be analyzed is passed from said inlet port to said outlet port;

means for irradiating said gas sample with light of predetermined frequency band as said respiratory gas sample passes through said gas sample chamber;

means for substantially simultaneously detecting an intensity, at each of more than n selected and differing wavelengths comprising said predetermined frequency band, of light substantially simultaneously emanating from said gas sample chamber as a result of irradiating said respiratory gas sample with said light of predetermined frequency band, wherein said more than n selected wavelengths of light are indicative of characteristic absorption wavelengths of said at least one of n anesthetic agent components, said detecting means including:

first means for filtering said light emanating from said gas sample chamber in a spatially distributed manner over a range of wavelengths included in the band of 7 to 10 microns, wherein each of said more than n wavelengths of light exit said first filtering means at a corresponding predefined one of a plurality of loci; and a plurality of detector means, each said detector means being positioned opposite a corresponding locus on said first filtering means to measure an intensity of a selected wavelength of light exiting said first filtering means at said corresponding locus;

second means for filtering said light emanating from said gas sample chamber to pass a selected passband of light in the range of 4 to 5 microns;;

means for determining a concentration of $CO_2$ in said gas sample based upon an intensity of said light passed by said second filtering means; and means for multi-variate statistically processing values corresponding with said plurality of selected intensities of said light exiting from said first filtering means to identify a concentration of said at least one of n anesthetic agent components.

2. The apparatus of claim 1 wherein said detecting means further comprises:

a memory;

means for simultaneously activating all of said plurality of detector means to concurrently create data indicative of said intensity at all said selected wavelengths of light;

means for storing each of said data in said memory.

3. The apparatus of claim 2 wherein a substantially linear relationship exists between concentration of said at least one of n anesthetic agent components contained in said gas sample and absorbance of said light of predetermined frequency band that irradiates said gas sample, said processing means comprises:

means for least squares processing of said concurrently created data stored in said memory and indicative of said intensity at all said selected wavelengths of light to calculate concentration of said at least one of n anesthetic agent components in said gas sample.

4. The apparatus of claim 2 wherein said processing means comprises a means for performing a partial least squares calculation on said concurrently created data stored in said memory and indicative of said intensity at all said selected wavelengths of light to calculate concentration of said at least one of n anesthetic agent components in said gas sample.

5. The apparatus of claim 1 wherein said multi-variate statistically processing means comprises a partial least squares processor receiving data from said detecting means representative of the intensity of light emanating from said gas sample chamber, as a result of irradiating said gas sample with said light of predetermined frequency band, at said more than n wavelengths, said partial least squares processor having at least one output, for outputting data indicative of a concentration of said at least one of n anesthetic agent components.

6. The apparatus of claim 1 wherein said first filtering means comprises a linear variable filter whose frequency response varies in at least one dimension along a length of said linear variable filter and wherein said plurality of detector means are configured in a linear array along said length of said linear variable filter.

7. The apparatus of claim 6 wherein said linear variable filter passes light of wavelength between 7.2 and 9.8 microns.

8. The apparatus of claim 6, wherein said linear variable filter is a wedge-shaped member having a plurality of tapered layers.

9. The apparatus of claim 1 wherein said filtering means passes narrow bands of light centered around said selected wavelengths.

10. The apparatus of claim 9 wherein said narrow bands of light passed by said first filtering means comprise a bandwidth of 0.69% of the centered wavelength.

11. The apparatus of claim 1 wherein said selected passband comprises a narrow band of light centered at a wavelength of 4.26 microns.

12. The apparatus of claim 1 wherein said second micron filtering means is juxtaposed to said first filtering means to together receive said light emanating from said gas sample chamber.

13. The apparatus of claim 12, wherein said plurality of detector means are configured in a linear array, and wherein said means for determining a concentration of $CO_2$ includes at least one detector juxtaposed in co-linear relation to said linear array, wherein detection of said light passed by said second filtering means is substantially simultaneous with detection by said plurality of detector means at each of said selected wavelengths.

14. A method for identifying the concentration of at least one of n anesthetic agent components contained in a respiratory gas sample, wherein each said anesthetic agent component has a unique pattern of spectral wavelength absorbance characteristics, n being a positive integer greater than zero, comprising the steps of:

passing through a gas sample chamber having an inlet port and an outlet port, a respiratory gas sample to be analyzed from said inlet port to said outlet port;

irradiating said gas sample with light of predetermined frequency band as said respiratory gas sample passes through said gas sample chamber;

detecting substantially simultaneously an intensity, at each of more than n selected and differing wavelengths comprising said predetermined frequency band, of light substantially simultaneously emanating from said gas sample chamber as a result of irradiating said respiratory gas sample with said light of predetermined frequency band, wherein said more than n selected wavelengths of light are indicative of characteristic absorption wavelengths of said at least one of n anesthetic agent components, said step of detecting including:

filtering said light emanating from said gas sample chamber in a spatially distributed manner over a range of wavelengths included in the band of 7 to 10 microns using a spatially varying filter, wherein each of said more than n wavelengths of light exit said spatially varying filter at a corresponding predefined one of a plurality of loci; and measuring substantially simultaneously using a plurality of detectors each positioned opposite a corresponding locus on said spatially varying filter, an intensity of a selected wavelength of light exiting said filter at said corresponding locus;

filtering said light emanating from said gas sample chamber to pass a selected passband of light in the range of 4 to 5 microns using a 4 to 5 micron filter;

determining a concentration of $CO_2$ in said gas sample based upon an intensity of said light passed in the range of 4 to 5 microns; and multi-variate statistically processing values corresponding with said plurality of detected intensities to identify a concentration of said at least one of n anesthetic agent components.

15. The method of claim 14 wherein said step of detecting further comprises:

simultaneously activating all of said plurality of detectors to concurrently create data indicative of said intensity at all said selected wavelengths of light; and storing each of said data in a memory.

16. The method of claim 15 wherein a substantially linear relationship exists between concentration of said at least one of n anesthetic agent components contained in said gas sample and absorbance of said light of predetermined frequency band that irradiates said gas sample, said processing step comprises:

least squares processing of said concurrently created data stored in said memory and indicative of said intensity at all said selected wavelengths of light to calculate concentration of said component in said gas sample.

17. The method of claim 16 wherein said processing step further comprises a partial least squares calculation on said concurrently created data stored in said memory and indicative of said intensity at all said selected wavelengths of light to calculate concentration of said at least one of n anesthetic agent components in said gas sample.

18. The method of claim 14 wherein said step of multivariate statistically processing comprises a partial least squares processor receiving data from said plurality of detectors representative of the intensity of light emanating from said gas sample chamber, as a result of irradiating said gas sample with said light of predetermined frequency band, at said more than n wavelengths, said partial least squares processor having at least one output, for outputting data indicative of a concentration of said at least one of n anesthetic agent components.

19. The method of claim 14 wherein said spatially varying filter comprises a linear variable filter whose frequency response varies in at least one dimension along a length of said linear variable filter and wherein said plurality of detectors are configured in a linear array along said length of said linear variable filter.

20. The method of claim 19 wherein said linear variable filter passes light of wavelength between 7.2 and 9.8 microns.

21. The method of claim 14 wherein said spatially varying filter means passes narrow bands of light centered around said selected wavelengths.

22. The method of claim 21 wherein said narrow bands of light passed by said filter comprise a bandwidth of 0.69% of the centered wavelength.

23. The method of claim 14 wherein said selected passband comprises a narrow band of light centered at a wavelength of 4.26 microns.

24. The method of claim 14 wherein said 4 to 5 micron filter is juxtaposed to said spatially varying filter to together receive said light emanating from said gas sample chamber.

* * * * *